United States Patent
Hahn et al.

(10) Patent No.: US 7,671,239 B2
(45) Date of Patent: Mar. 2, 2010

(54) METHOD AND APPARATUS FOR PRODUCING PURIFIED METHYL ISOBUTYL KETONE

(75) Inventors: Tristan Erich Hahn, Johannesburg (ZA); Johannes Jochemus Gildenhuys, Johannesburg (ZA); Braam Van Dyk, Sasolburg (ZA); James Christoffel Crause, Sasolburg (ZA); Paranjothi Moodliar, Johannesburg (ZA)

(73) Assignee: Sasol Technology (Pty) Limited, Johannesburg (ZA)

( * ) Notice: Subject to any disclaimer, the term of this patent is extended or adjusted under 35 U.S.C. 154(b) by 0 days.

(21) Appl. No.: 12/085,990

(22) PCT Filed: Nov. 27, 2006

(86) PCT No.: PCT/IB2006/054454

§ 371 (c)(1),
(2), (4) Date: May 8, 2009

(87) PCT Pub. No.: WO2007/069109

PCT Pub. Date: Jun. 21, 2007

(65) Prior Publication Data

US 2009/0253940 A1 Oct. 8, 2009

(30) Foreign Application Priority Data

Dec. 14, 2005 (ZA) .............................. 2005/10182

(51) Int. Cl.
*C07C 45/82* (2006.01)
*C07C 45/84* (2006.01)

(52) U.S. Cl. ..................................... 568/388

(58) Field of Classification Search .................. 568/388
See application file for complete search history.

(56) References Cited

U.S. PATENT DOCUMENTS

| 3,574,763 | A | 4/1971 | Wollner et al. |
| 3,953,517 | A | 4/1976 | Schmitt et al. |
| 2003/0065227 | A1 | 4/2003 | Saayman et al. |

OTHER PUBLICATIONS

Onoue et al.; "Why Not Do It In One Step? The Case of MIBK", Chemtech, XP009084353, pp. 36-39, (1977).
Ai et al.; "Process for Separating Methylisobutanone Synthesized From Acetone", Abstract of CN 1 331 070, XP-002435247, (2002).

*Primary Examiner*—Sikarl A Witherspoon
(74) *Attorney, Agent, or Firm*—Finnegan, Henderson, Farabow, Garrett & Dunner, L.L.P.

(57) ABSTRACT

This invention relates to a method of producing purified methyl isobutyl ketone (MIBK) comprising subjecting a feed stream containing MIBK and impurities to a first distillation procedure from which acetone is recovered. The bottom product of the first distillation procedure is fed to a liquid-liquid separator and an organic phase from the said liquid-liquid separator is fed to the top region of a second distillation column to produce an overhead product. The said overhead product is condensed and fed to the said liquid-liquid separator. A bottom product containing MIBK is withdrawn from the second distillation column. This bottom product is fed to a third distillation column, high boiling impurities are withdrawn as a bottom product, and purified MIBK is also withdrawn. The invention also relates to an apparatus used in such a method.

11 Claims, 1 Drawing Sheet

METHOD AND APPARATUS FOR PRODUCING PURIFIED METHYL ISOBUTYL KETONE

CROSS REFERENCE TO RELATED APPLICATION

Figure 1:
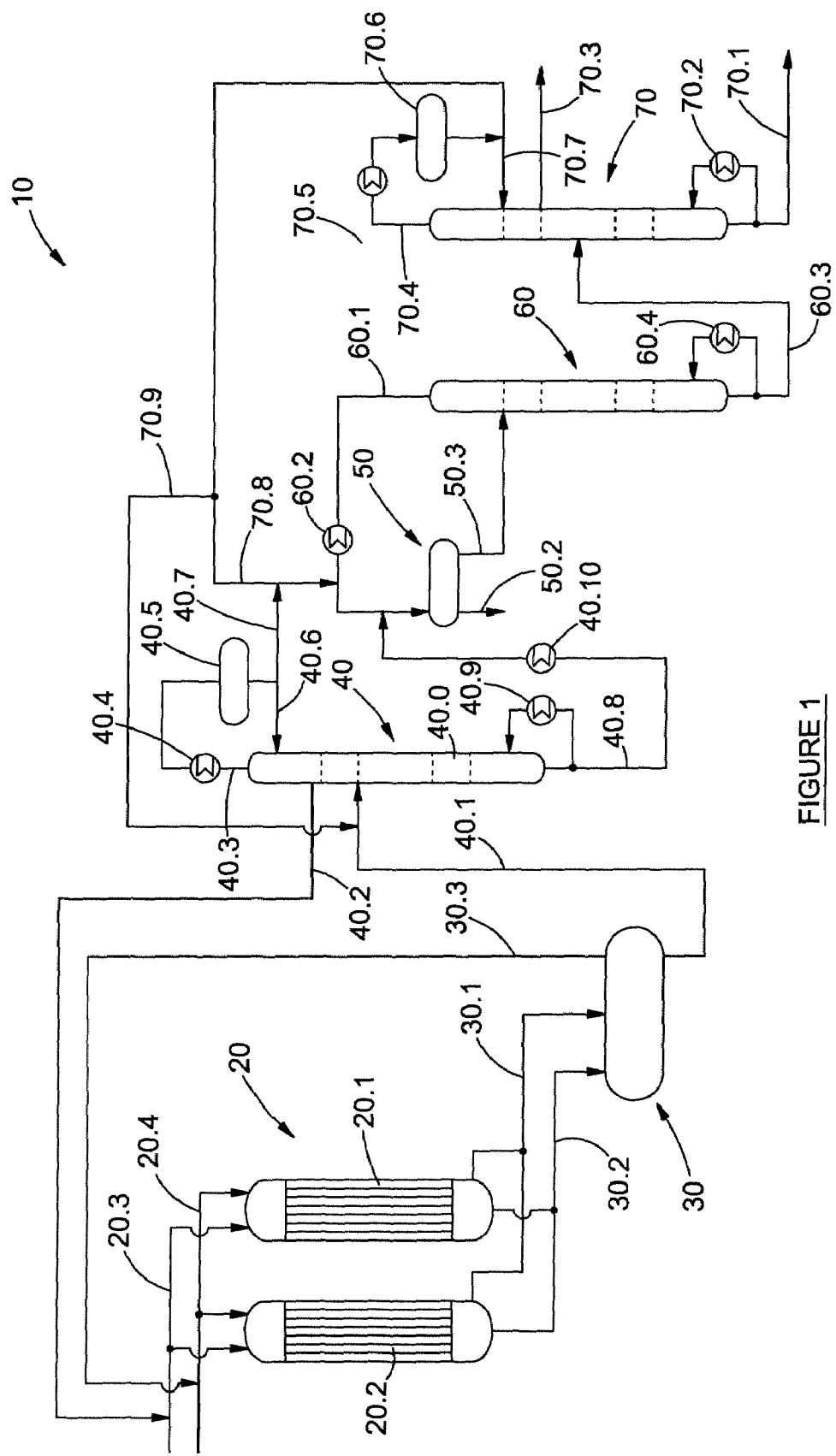

This application is a national phase application based on PCT/IB2006/054454, filed Nov. 27, 2006, and claims the priority of South African Application No. 2005/10182, filed Dec. 14, 2005, the content of both of which is incorporated herein by reference.

TECHNICAL FIELD

This invention relates to a method of producing purified methyl isobutyl ketone (MIBK). The invention also relates to an apparatus for use in such a method.

BACKGROUND ART

Processes which include condensation of one or more carbonyl-containing reactants to form an unsaturated carbonyl-containing compound, and hydrogenation of said unsaturated compound to a saturated carbonyl-containing product, are well known.

One such process is the preparation of methyl isobutyl ketone (MIBK) from acetone. In this process condensation of two acetone molecules yield diacetone alcohol (DAA) which is dehydrated to yield mesityl oxide (MSO), and the MSO is hydrogenated to MIBK. The condensation and dehydration reaction takes place in the presence of an acidic catalyst, and the hydrogenation takes place in the presence of a hydrogenation catalyst such as a noble metal.

The production of MIBK can take place in two process steps as indicated above or in a single process step in the presence of a single condensation and hydrogenation catalyst. Such single step processes are disclosed in, for example, U.S. Pat. No. 3,574,763; EP 1 32 1 450 and South African complete patent application number 2004/8988.

The MIBK produced from the condensation and hydrogenation of acetone includes one or more impurities such as propane, isobutane, methyl pentane, acetone, 2-propanol, water, diacetone alcohol (DAA), mesityl oxide (MSO) and high boiling compounds such as diisobutyl ketone, C9 paraffins and ketones.

Methods of purifying MIBK are also known in the art. The article "Why not do it in one step", Chemtech, January 1977 discloses a process wherein the MIBK reaction products are subjected to a gas separator to remove unreacted hydrogen for recycle to the MIBK reactor. The liquid from the gas separator is fed to a first distillation column where acetone is recovered as an overhead product and recycled to the MIBK reactor. The bottom product of the first column is then fed to a liquid-liquid separator (decanter), where the aqueous phase is removed from the process and the organic phase is fed to a second distillation column somewhere between the take-off of the bottom product and a reflux entry position. An overhead low boiling product is removed as distillate in the second column. The bottom product of the second column is then fed to a third distillation column where high boiling compounds are removed as the bottom product and MIBK is removed as the distillate.

"Methyl Isobutyl Ketone by Direct Condensation of Acetone", SRI Reports, May 1972, discloses a similar process as described above. The main difference is that the first distillation column described above is replaced by two columns, namely a first distillation column where low boiling products (particularly methyl pentane as an azeotrope with acetone) are removed as a distillate. The bottom product is then fed to a second column where the unreacted acetone is removed as a distillate and recycled to the MIBK reactor. Another difference is that the third column (similar function as the second column above) is fitted with an overheads decanter.

DISCLOSURE OF THE INVENTION

Method

According to a first aspect of the present invention there is provided a method of producing purified methyl isobutyl ketone (MIBK) comprising:

subjecting a feed stream containing MIBK and impurities in the form of at least water and organic compounds (including unreacted acetone) from a condensation and hydrogenation reaction of acetone to a first distillation procedure from which at least acetone is recovered, and a bottom product containing MIBK and impurities is withdrawn;

feeding the bottom product of the first distillation procedure to a liquid-liquid separator associated with a second distillation column in which liquid-liquid separator an organic phase and an aqueous phase separate; feeding the organic phase from the said liquid-liquid separator to the top region of a second distillation column which column produces an overhead product; condensing the said overhead product; feeding the resulting condensed overhead product to the same liquid-liquid separator to which the bottom product of the first distillation procedure is fed; and withdrawing a bottom product containing MIBK and high boiling impurities from the bottom of the second column;

feeding the bottom product of the second distillation column to a third distillation column; withdrawing high boiling impurities as a bottom product; and withdrawing purified MIBK from said third distillation column.

The method may also include a step of producing MIBK, preferably by condensation and hydrogenation of acetone to provide the feed stream containing MIBK and impurities in the form of at least water and organic compounds (including unreacted acetone).

MIBK Production

The MIBK may be produced by any known process, but preferably it is produced in the presence of a single condensation and hydrogenation catalyst (e.g. a palladium based resin catalyst) preferably in a single process step. The MIBK may be produced as described in South African complete patent application number 2004/8988. The MIBK may be produced by feeding acetone and hydrogen to a suitable reactor such as a tubular reactor, preferably a tubular trickle bed reactor.

Hydrogen Removal

The method may also include a step of removing hydrogen from the feed stream containing MIBK and impurities from the condensation and hydrogenation reaction of acetone. The hydrogen will usually be unreacted hydrogen from the condensation and hydrogenation of acetone to produce MIBK. The hydrogen may be removed at any suitable stage, preferably prior to the first distillation procedure. The hydrogen may be removed by means of a hydrogen separator, preferably a hydrogen separation drum, and the removed hydrogen may be recycled to the MIBK production step.

First Distillation Procedure

The first distillation procedure may be carried out in one or more distillation columns and preferably low boiling impurities are withdrawn separately from recovered acetone. Preferably the first distillation procedure is carried out in a single first distillation column by feeding the feed stream containing MIBK and impurities to the first distillation column wherein low boiling impurities are withdrawn as an overhead product; acetone is withdrawn as a side draw, and MIBK and impurities are withdrawn as a bottom product.

The overhead product of this column will usually contain compounds such as propane, isobutane, methyl pentane and some acetone. The overhead product may be refluxed. In one embodiment of the invention the overhead product may be condensed and may be fed to a reflux drum from which some overhead product is refluxed and some is discharged.

The acetone recovered (preferably as a side draw) may be recycled to the MIBK production step.

The withdrawn bottom product usually contains MIBK and high boiling impurities. The impurities may include acetone, 2-propanol, water and higher boiling compounds. The MIBK content at this stage may be in the region of 80 wt %.

Liquid-Liquid Separation and the Second Distillation Column

The bottom product of the first distillation procedure may be cooled prior to feeding it to the liquid-liquid separator.

The organic phase of the liquid-liquid separator may be fed as reflux to the top region of the second column. The aqueous phase from the liquid-liquid separator may be withdrawn, may be discharged and may be fed to a water recovery unit.

The liquid-liquid separator may comprise a decanter.

The overhead product of the second column is condensed preferably in a condenser, prior to feeding it to the liquid-liquid separator.

It will be appreciated that acetone, 2-propanol, water and some MIBK will usually report to the overhead product of the second column as a heterogeneous azeotrope. The organic phase of the liquid-liquid separator is then refluxed to the second column to recover the MIBK. The acetone and 2-propanol report to the aqueous phase of the liquid-liquid separator.

The bottom product of the second column will now be rich in MIBK.

Third Distillation Column

Preferably the purified MIBK is withdrawn as a side draw in the third column (preferably in the rectification section thereof) and low boiling impurities are withdrawn as an overhead product. The MIBK may have a purity as high as 99.5 wt %.

The overhead product of the third column may include MIBK and low boiling decomposition products.

The overhead product of the third column may be condensed and may be fed to a reflux drum. The condensed overhead product may be recycled to the liquid-liquid separator associated with the overhead product of the second column, alternatively or additionally it may be combined with the feed to the first separation procedure. Alternatively or additionally at least part of the condensed overhead product may be refluxed.

The bottom product of the third column contains high boiling impurities and may be treated as waste product.

Apparatus

According to a second aspect of the present invention there is provided an apparatus suitable for producing purified methyl isobutyl ketone (MIBK) comprising:

a first distillation apparatus which includes a feed line for feeding a feed stream containing MIBK and impurities in the form of at least water and organic compounds (including acetone) from a condensation and hydrogenation reaction of acetone to the first distillation apparatus, the first distillation apparatus further including an acetone take-off for withdrawing acetone, and a bottom product take-off for withdrawing a bottom product in the form of MIBK and impurities from the bottom of the first distillation apparatus;

a liquid-liquid separator associated with a second distillation column which liquid-liquid separator in use allows an organic phase and an aqueous phase to separate; the liquid-liquid separator including a feed line for feeding the bottom product of the first distillation apparatus to the said liquid-liquid separator;

a second distillation column which includes a feed line for feeding the organic phase from the liquid-liquid separator to the top region of the second distillation column; the second distillation column further including an overhead take-off for withdrawing an overhead product in the form of low boiling compounds; a condenser for condensing the said overhead product; a feed line for feeding the condensed overhead product to the liquid-liquid separator; and the second distillation column further including a bottom product take-off for withdrawing a bottom product in the form of MIBK and high boiling impurities from the bottom of the second distillation column;

a third distillation column which includes a feed line for feeding the bottom product of the second distillation column to the third distillation column, a bottom product take-off for withdrawing high boiling impurities as a bottom product; and a MIBK take-off for withdrawing purified MIBK from the third distillation column.

The apparatus may also include a reactor for producing MIBK, preferably by condensation and hydrogenation of acetone to produce the feed stream containing MIBK and impurities in the form of at least water and organic compounds (including acetone).

MIBK Reactor

The MIBK reactor may comprise any suitable MIBK reactor, preferably a reactor for producing MIBK in the presence of a single condensation and hydrogenation catalyst (e.g. a palladium based resin catalyst), preferably in a single process step. The MIBK reactor may comprise a tubular reactor, preferably a tubular trickle bed reactor with one or more feed lines for feeding acetone and hydrogen to the reactor.

Hydrogen Separator

The apparatus may also include means for removing hydrogen from the feed stream containing MIBK and impurities from the condensation and hydrogenation reaction of acetone. The means for removing hydrogen may comprise a hydrogen separator, preferably a hydrogen separator drum and may be located before the first distillation apparatus.

A hydrogen recycle feed line may be provided to feed the recovered hydrogen from the hydrogen separator to the hydrogen feed line to the MIBK reactor.

First Distillation Apparatus

The first distillation apparatus may comprise one or more distillation columns and preferably it includes an overhead product take-off for withdrawing low boiling impurities separately from the acetone take-off. Preferably the first distillation apparatus comprises a single first distillation column which preferably includes the feed line for the feed stream containing MIBK and impurities; an overhead product take-off for withdrawing low boiling impurities; an acetone take-off for withdrawing acetone as a side draw; and a bottom product take-off for withdrawing a bottom product in the form of MIBK and impurities.

The first distillation apparatus may also include a condensor for condensing the overhead product. The first distillation apparatus may also include a reflux drum for receiving the condensed overhead product and a feed line for feeding at least part of the condensed overhead product from the reflux drum as reflux to the first distillation apparatus. The reflux drum may also include a discharge line for discharging at least some of the condensed overhead product from the reflux drum.

The first distillation apparatus may include a recycle line for recycling acetone withdrawn from the first distillation column to the MIBK reactor.

Liquid-Liquid Separator at the Second Distillation Column

The feed line for feeding the bottom product of the first distillation apparatus, preferably includes a cooler for cooling the bottom product of the first distillation apparatus prior to being fed to the liquid-liquid separator.

The liquid-liquid separator associated with the second distillation column may comprise a decanter.

The feed line for feeding the organic phase from the liquid-liquid separator to the second column preferably feeds the said organic phase of the liquid-liquid separator as reflux to the top region of the second column. The liquid-liquid separator may also include a take-off line for removing the aqueous phase.

Third Distillation Column

Preferably the MIBK take-off from the third distillation column withdraws purified MIBK as a side draw, and preferably the third distillation column includes an overhead product take-off for withdrawing low boiling impurities.

The overhead take-off of the third distillation column may be connected to a condenser, which in turn may be connected to a reflux drum. The reflux drum may include feed lines to one or more of the following i) the top of the third distillation column, ii) the liquid-liquid separator and iii) the feed line of the first column.

EXAMPLE

The invention will now be further described by means of the following non-limiting example wherein:

FIG. 1 is a diagrammatic representation of an apparatus for producing purified MIBK according to the present invention.

An apparatus 10 for producing purified MIBK comprises a reactor 20 for producing MIBK by condensation and hydrogenation of acetone; a hydrogen separator 30; a first distillation apparatus 40; a liquid-liquid separator 50; a second distillation column 60 and a third distillation column 70.

The reactor 20 for producing MIBK comprises two tubular trickle bed reactors 20.1 and 20.2 for producing MIBK from acetone and hydrogen in the presence of a single condensation and hydrogenation catalyst (e.g. a palladium based resin catalyst) and in a single step. The reactors 20.1 and 20.2 include an acetone feed line 20.3 and a hydrogen feed line 20.4.

Vapour product from the reactors 20.1 and 20.2 are fed to the hydrogen separator 30 via feed line 30.1 while liquid product from the reactors 20.1 and 20.2 are fed to the hydrogen separator 30 via feed line 30.2. The hydrogen separator 30 is a hydrogen separation drum. A hydrogen recycle feed line 30.3 feeds recovered hydrogen to the hydrogen feed line 20.4.

The MIBK reactor 20 and hydrogen separator 30 are well known in the art and accordingly are not described in detail in this specification. The MIBK reactors 20.1 and 20.2 may be operated at 120° C. and 30 barg (3000 kPa).

The first distillation apparatus 40 comprises a single first distillation column 40.0 and includes a feed line 40.1 for feeding the product from the hydrogen separator 30 to the first column 40.0. The product in the feed line 40.1 in use contains MIBK and impurities in the form of at least water and organic compounds. The organic compounds comprise organic compounds (including acetone) from the condensation and hydrogenation reaction of acetone.

The first distillation column 40.0 also includes an acetone take-off 40.2 for withdrawing acetone as a side draw. The acetone take-off 40.2 also serves as a recycle line for recycling the recovered acetone to the acetone feed line 20.3.

The first distillation column 40.0 further includes an overhead product take-off 40.3 for withdrawing low boiling impurities separately from the acetone take-off 40.2. The overhead vapour product take-off 40.3 feeds the overhead product to a condenser 40.4 and the condensed overhead product is then fed to a reflux drum 40.5 from which some of the condensed overhead product is refluxed via feed line 40.6 to the top region of the column 40.0 and some overhead product is discharged via line 40.7. The overhead product usually includes compounds such as propane, isobutane, methyl pentane and some acetone.

The first distillation column 40.0 also includes a bottom product take-off 40.8 for withdrawing a bottom product in the form of MIBK and impurities from the bottom of the first distillation column 40.0. The impurities may include acetone, 2-propanol, water and higher boiling compounds. The MIBK content at this stage may be in the region of 80 wt %. The column 40.0 is also equipped with a reboiler 40.9.

The bottom product in take-off 40.8 is fed to a cooler 40.10 prior to it being fed to the liquid-liquid separator 50.

The liquid-liquid separator 50 is associated with the second distillation column 60 and comprises a decanter 50 wherein an organic phase and an aqueous phase separates. The aqueous phase from the decanter 50 is discharged through line 50.2 while the organic phase is fed as feed and reflux to the second distillation column 60 via line 50.3.

The second distillation column 60 includes an overhead take-off 60.1 for withdrawing an overhead product. The take-off 60.1 feeds the overhead product to a condensor 60.2 which condenses the overhead product, and which condensed overhead product is then fed to the decanter 50.

It will be appreciated that acetone, 2-propanol, water and some MIBK will usually report to the overhead product of the column 60 as a heterogeneous azeotrope. The MIBK primarily reports to the organic phase of the decanter 50 which is refluxed to the column 60 while acetone and 2-propanol primarily report to the aqueous phase of the decanter 50 which aqueous phase is discharged.

The second distillation column further includes a bottom product take-off 60.3 for withdrawing a bottom product in the form of MIBK and high boiling impurities from the bottom of the second column 60. The column 60 is also fitted with a reboiler 60.4.

The bottom product take-off 60.3 serves as a feed line for feeding the bottom product of the second column 60 to the third distillation column 70. The third distillation column 70 includes a bottom product take-off 70.1 for withdrawing and discharging high boiling impurities as a bottom product and the column 70 is fitted with a reboiler 70.2.

The third column 70 also includes a MIBK take-off 70.3 to withdraw purified MIBK as a sidedraw in the rectification section of the column 70. The MIBK may have a purity of at least 99.5 wt % MIBK. An overhead product take-off 70.4 withdraws low boiling impurities as an overhead product. The overhead vapour product take-off 70.4 feeds the overhead product to a condenser 70.5 where the overhead product is condensed. The condensed overhead product is then fed to a reflux drum 70.6 from which part of the condensed overhead product is refluxed to the top section of column 70 via line 70.7 and part is recycled either to the decanter 50 via line 70.8, or the first column 40.0 via line 70.9.

It will be appreciated that the conditions under which the columns 40.0, 60 and 70 are operated would be known to a person skilled in the art and accordingly they are not described in this specification.

In one specific example the apparatus as set out in FIG. 1 was used, with stream 70.9 disabled. The key operating conditions are set out in Table 1 and the key stream compositions are set out in Table 2.

TABLE 1

OPERATING CONDITIONS

| Columns | 40 | 60 | 70 |
|---|---|---|---|
| Bottoms temperature (deg C.) | 101 | 136 | 166 |
| Bottoms pressure (barg) | 0.85 | 0.85 | 0.85 |

| Phase separator | | 50 | |
|---|---|---|---|
| Temperature (deg C.) | | 70 | |
| Pressure (barg) | | 0.55 | |

1 barg is 100 Kpa

TABLE 2

| STREAM NUMBER | 40.1 | 40.8 | 60.3 | 70.3 |
|---|---|---|---|---|
| | MASS FRACTION | | | |
| Acetone | 0.705 | 0.007 | 0.000 | 0.001 |
| 2 Methyl Pentane | 0.003 | 0.000 | 0.000 | 0.000 |
| MIBK | 0.222 | 0.802 | 0.961 | 0.998 |
| Di-isobutyl Ketone | 0.005 | 0.017 | 0.020 | 0.000 |
| Water | 0.058 | 0.157 | 0.000 | 0.000 |
| Other | 0.006 | 0.017 | 0.018 | 0.001 |

The invention claimed is:

1. A method of producing purified methyl isobutyl ketone (MIBK) comprising:

subjecting a feed stream containing MIBK and impurities in the form of at least water and organic compounds (including unreacted acetone) from a condensation and hydrogenation reaction of acetone to a first distillation procedure from which at least acetone is recovered, and a bottom product containing MIBK and impurities is withdrawn;

feeding the bottom product of the first distillation procedure to a liquid-liquid separator associated with a second distillation column in which liquid-liquid separator an organic phase and an aqueous phase separate; feeding the organic phase from said liquid-liquid separator to the top region of a second distillation column which column produces an overhead product; condensing said overhead product; feeding the resulting condensed overhead product to the same liquid-liquid separator to which the bottom product of the first distillation procedure is fed; and withdrawing a bottom product containing MIBK and high boiling impurities from the bottom of the second column;

feeding the bottom product of the second distillation column to a third distillation column; withdrawing high boiling impurities as a bottom product; and withdrawing purified MIBK from said third distillation column.

2. The method of claim 1 which includes a step of producing MIBK by condensation and hydrogenation of acetone to provide the feed stream containing MIBK and impurities in the form of at least water and organic compounds (including unreacted acetone).

3. The method of claim 2 wherein the MIBK is produced in the presence of a single condensation and hydrogenation catalyst in a single process step.

4. The method of claim 1 which includes a step of removing hydrogen from the feed stream containing MIBK and impurities from the condensation and hydrogenation reaction of acetone.

5. The method of claim 4 wherein the hydrogen is removed prior to the first distillation procedure.

6. The method of claim 1 wherein the first distillation procedure is carried out in one or more distillation columns; and low boiling impurities are withdrawn separately from the recovered acetone.

7. The method of claim 6 wherein the first distillation procedure is carried out in a single first distillation column by feeding the feed stream containing MIBK and impurities to the first distillation column wherein low boiling impurities are withdrawn as an overhead product; acetone is withdrawn as a side draw; and MIBK and impurities are withdrawn as a bottom product.

8. The method of claim 7 wherein the overhead product is refluxed.

9. The method of claim 2 wherein the acetone recovered is recycled to the step of producing MIBK.

10. The method of claim 1 wherein the purified MIBK is withdrawn as a side draw in the third column; and low boiling impurities are withdrawn as an overhead product.

11. The method of claim 10 wherein the overhead product of the third column is condensed and is fed to a reflux drum.

* * * * *